(12) United States Patent
Bernhardt et al.

(10) Patent No.: US 6,821,545 B2
(45) Date of Patent: Nov. 23, 2004

(54) LOW CALORIE FAT MATERIALS THAT ELIMINATE LAXATIVE SIDE EFFECT

(75) Inventors: Christian Albert Bernhardt, Fairfield, OH (US); Harry Madison Taylor, Cincinnati, OH (US)

(73) Assignee: Procter & Gamble, Cincinnati, OH (US)

(*) Notice: Subject to any disclaimer, the term of this patent is extended or adjusted under 35 U.S.C. 154(b) by 356 days.

(21) Appl. No.: 07/153,880

(22) Filed: Feb. 9, 1988

(65) Prior Publication Data

US 2001/0003119 A1 Jun. 7, 2001

Related U.S. Application Data

(63) Continuation of application No. 07/022,191, filed on Mar. 5, 1987, now abandoned, which is a continuation-in-part of application No. 06/831,737, filed on Feb. 20, 1986, now abandoned.

(51) Int. Cl.$^7$ .............................................. A23D 9/007
(52) U.S. Cl. .......................... 426/611; 426/804; 536/23
(58) Field of Search .................................. 426/611, 804; 536/23

(56) References Cited

U.S. PATENT DOCUMENTS

| | | | |
|---|---|---|---|
| 3,158,490 A | | 11/1964 | Baur et al. |
| 3,600,189 A | | 8/1971 | Mattson et al. |
| 3,649,647 A | | 3/1972 | Ota et al. |
| 4,005,195 A | | 1/1977 | Jandacek |
| 4,005,196 A | | 1/1977 | Jandacek et al. |
| 4,034,083 A | | 7/1977 | Mattson |
| 4,508,746 A | | 4/1985 | Hamm |
| 4,626,441 A | | 12/1986 | Wolkstein |
| 4,789,664 A | | 12/1988 | Seligson et al. |
| 4,797,300 A | | 1/1989 | Jandacek et al. |
| 4,835,001 A | | 5/1989 | Mijac et al. |
| 4,880,657 A | | 11/1989 | Guffey et al. |
| 4,940,601 A | * | 7/1990 | Orphanos et al. ............ 426/601 |
| 4,942,054 A | * | 7/1990 | Winter et al. ................ 426/611 |
| 4,943,563 A | * | 7/1990 | Mutschler et al. ............ 514/23 |
| 4,952,687 A | * | 8/1990 | Bodor et al. .................. 514/23 |

FOREIGN PATENT DOCUMENTS

| | | |
|---|---|---|
| EP | 0233856 | 8/1987 |
| EP | 0236288 | 9/1987 |
| EP | 0235836 | 11/1987 |
| EP | 0287157 | 10/1988 |
| EP | 0287158 | 10/1988 |
| EP | 0290065 | 11/1988 |
| EP | 0290216 | 11/1988 |
| EP | 0290420 | 11/1988 |
| EP | 0290421 | 11/1988 |
| EP | 0311154 | 4/1989 |

OTHER PUBLICATIONS

Mattson et al., "The Effect of a Non–Absorbable Fat . . . ", *J. Nutrition* 109, #10, pp. 1688–1693 (Oct. 1979).
Mattson et al., "The Effect of a Non–Absorbable Lipid . . . ", *J. Nutrition*, 106, #6, pp. 747–752 (Jun. 1976).
Fallat et al., "Short Term Study of Sucrose Polyester . . . ", *Am. J. Clin. Nutr.*, 29, pp. 1204–1215 (Nov. 1976).
Olestra Food Additive Petition (Procter & Gamble), Filed with the F.D.A., available to the public on May 7, 1987, pp. 1, 3, 21, 22, 23, 24, 31, 32 and 56.
*Analytical Chemistry*, vol. 57, No. 12, Oct. 1985 (Chester et al.), pp. 2243–2247.
Freling, "Monitor Batch Quality with Rheograms", *Instrumentation Technology*, pp. 41–45 (Jun. 1972).
Beckman, "Instructions for Using the SW 60 Ti Rotor", Beckman Instruments, Palo Alto, CA, pp. 1–10 (1984).
Idson, "Rheology: Fundamental Concepts", *Cosmetics and Toiletries*, vol. 93, pp. 23–26 and 28–30 (Jul. 1978).
Idson, "Rheology: Fundamental Concepts", *Cosmetics and Toiletries*, vol. 93, Jul. 1978, pp. 23–30.
Weiss, Food Oils and Their Uses, Avi Publishing Co., Westport, CT, 2nd edition, pp. 16, 195–197 (1983).

* cited by examiner

*Primary Examiner*—Carolyn Paden
(74) *Attorney, Agent, or Firm*—Carl J. Roof

(57) ABSTRACT

The present invention is a composition of matter comprising an edible, wholly or partially nondigestible low calorie fat material having a non-Newtonian pseudoplastic rheology at body temperature. In particular, at 100° F. (37.8° C.) the fat material has: (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$; (b) a yield point of at least about 2,500 dynes/cm$^2$; (c) a thixotropic area of at least about 0.20×10$^6$ dynes/cm$^2$-sec.; and (d) a liquid/solid stability of at least about 50%.

The composition is useful as a substitute for triglyceride fats in low calorie fat-containing food products, and as a method for reducing serum cholesterol.

Examples of specific low calorie fat materials that can be used in this invention include sugar fatty acid polyesters, polyglycerol fatty acid polyesters, and tricarboxylic acids esterified with fatty alcohols.

18 Claims, No Drawings

LOW CALORIE FAT MATERIALS THAT ELIMINATE LAXATIVE SIDE EFFECT

RELATED APPLICATIONS

This application is continuation-in-part of application U.S. Ser. No. 06/831,737, filed Feb. 20, 1986, now abandoned, which is a continuation of application Ser. No. 07/022,191, filed Mar. 5, 1987, now abandoned.

FIELD OF THE INVENTION

This invention relates to compositions useful as low calorie fat materials. The invention further relates to the fat materials in low calorie foods and as a method for reducing serum cholesterol.

BACKGROUND OF THE INVENTION

One of the most common metabolic problems among people today is obesity. This condition is primarily due to ingestion of a greater number of calories than are expended. Fat is the most concentrated form of energy in the diet, with each gram of fat supplying approximately 9 calories. Overall, fat constitutes about 40% of the total calories in the diet.

Triglycerides constitute about 90% of the total fat consumed in the average diet. One method by which the caloric value of edible fat could be lowered would be to decrease the amount of triglyceride that is absorbed in the human system since the usual edible triglyceride fats are almost completely absorbed (see *Lipids*, 2, H. J. Deuel, Interscience Publishers, Inc., New York 1955, page 215). A low calorie fat offers a convenient and practical method by which obesity can be prevented or overcome.

An Executive Summary prepared by the Committee on Diet, Nutrition and Cancer, National Academy of Sciences, National Academy Press, Washington, D.C., pp. 4–5 (1982), discusses a possible link between cancer and the intake of fat, i.e., total dietary fat, saturated fat, polyunsaturated fat, and cholesterol. Epidemiological studies have repeatedly shown an association between dietary fat and the occurrence of cancer at several sites, especially the breast, prostate, and large bowel. The data are not entirely consistent, however. Like epidemiological studies, numerous experiments in animals have shown that dietary fats influence tumorigenesis, especially in the breast and the colon.

Pathological conditions which can afflict warmblooded animals can involve the absorption of cholesterol, and associated hypercholesterolemia. For example, epidemiological studies have demonstrated with few exceptions that populations consuming large quantities of saturated fat and cholesterol have a relatively high concentration of serum cholesterol and a high mortality from coronary heart disease. Conversely, the serum cholesterol levels and the mortality from coronary disease are low in populations with a low consumption of saturated fat and cholesterol.

The National Institutes of Health Consensus Development Conference published "Lowering Blood Cholesterol to Prevent Heart Disease", in JAMA, Vol. 253, No. 14, pp. 2080–2086 (1985). It was concluded that elevation of blood cholesterol levels is a major cause of coronary artery disease, and that lowering definitely elevated blood cholesterol levels (specifically, blood levels of low-density lipoprotein [LDL] cholesterol) will reduce the risk of heart attacks caused by coronary heart disease. The Panel recommended appropriate changes in the diet, particularly a reduction in the amount of fat eaten, in order to reduce blood serum cholesterol levels.

Hence, there is a need for ways to reduce the amount of triglyceride fat in the diet, in order to reduce the risks of obesity, cancer, and heart disease.

Low calorie fats which can replace triglycerides are described by Mattson et al. U.S. Pat. No. 3,600,186 to Mattson et al. discloses low calorie, fat-containing, food compositions in which at least a portion of the triglyceride content is replaced with a polyol fatty acid ester, said polyol fatty acid ester having at least four fatty acid ester groups with each fatty acid having from 8 to 22 carbon atoms.

U.S. Pat. No. 4,005,196 to Jandacek et al. discloses the low calorie fat-containing food compositions of the Mattson et al. patent, in combination with sufficient fat-soluble vitamin selected from the group consisting of vitamin A, vitamin D, vitamin E and vitamin K.

U.S. Pat. No. 3,954,976 to Mattson et al. describes pharmaceutical compositions for inhibiting the absorption of cholesterol comprising effective unit dosage amounts of a polyol fatty acid ester having at least four fatty acid ester groups, and a method for treating and/or preventing hypercholesterolemia in an animal comprising systematically administering to such animal successive therapeutically effective doses of said polyol fatty acid ester.

The esters disclosed in the Mattson et al. and Jandacek et al. patents are effective fat substitutes for use in low calorie food products or in pharmaceutical compositions for controlling hypercholesterolemia. Unfortunately, regular ingestion of moderate to high levels of these esters can produce an undesirable "laxative" effect, namely, leakage of the ester through the anal sphincter. One way to prevent this undesirable laxative effect is to formulate the esters so that they are completely solid at body temperature.

Another means of preventing the undesirable laxative effect is through the addition to the ester of anti-anal leakage agents such as those described in U.S. Pat. No. 4,005,195 to Jandacek. This patent discloses anti-anal leakage agents which include solid fatty acids (melting point 37° C. or higher) and their triglyceride source, and solid polyol fatty acid polyesters. Specifically, the agents are selected from the group consisting of: edible $C_{12}$ and higher saturated fatty acids, and their edible salts; edible, digestible sources of $C_{12}$ and higher saturated fatty acids; edible, nonabsorbable, nondigestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, nondigestible esters of alpha-branched chain $C_{10}$–$C_{18}$ fatty acids.

Completely solid esters, and solid triglycerides or esters used as anti-anal leakage agents, have drawbacks when used in low calorie food compositions. An ester or triglyceride having a high solids content tastes "waxy" in the mouth when ingested. It would be desirable to have a low calorie fat material that is still effective at reducing calories and cholesterol, and that can also have a relatively low solids content so that it does not taste waxy in the mouth. At the same time, it is critical that this fat material not produce an undesirable laxative side effect.

It is therefore an object of the present invention to provide a low calorie fat material for use in low calorie food compositions and as a method for reducing serum cholesterol.

It is another object of this invention to provide a fat material that does not cause a laxative side effect.

It is a further object of this invention to avoid the laxative side effect without the need for use of added anti-anal leakage agents.

These and other objects of the invention will be made clear by the disclosure herein.

SUMMARY OF THE INVENTION

The present invention is a composition of matter comprising an edible, wholly or partially nondigestible low calorie fat material having a non-Newtonian pseudoplastic rheology at body temperature. In particular, at 100° F. (37.8° C.) the fat material has: (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$; (b) a yield point of at least about 2,500 dynes/cm$^2$; (c) a thixotropic area of at least about 0.20×10$^6$ dynes/cm$^2$-sec.; and (d) a liquid/solid stability of at least about 50%.

The composition is useful as a substitute for triglyceride fats in low calorie fat-containing food products, and as a method for reducing serum cholesterol.

Examples of specific low calorie fat materials that can be used in this invention include sugar fatty acid polyesters, polyglycerol fatty acid polyesters, and tricarboxylic acids esterified with fatty alcohols.

DETAILED DESCRIPTION OF THE INVENTION

By "low calorie fat materials" is meant edible materials which can replace triglyceride fats or oils in the human diet. These materials provide the benefits of triglyceride fats and oils, i.e., lubricity and flavors.

By "wholly nondigestible" is meant that substantially all of the material is not digested by the body. It passes through the digestive system substantially the same as when it was ingested. The term "partially nondigestible" means that at least about 30% of the material is not digested. Preferably at least about 70% of the material is not digested.

By "liquid/solid stability" as used herein is meant that the liquid portion of the material does not readily separate from the solid portion at body temperature, i.e., the material appears to be a solid even though up to about 95% of it is liquid. Liquid/solid stability is measured by centrifuging a sample of the material at 60,000 rpm for one hour at 100° F. (37.8° C.). Liquid/solid stability is defined as: 100% minus percentage of the material that separated as a liquid after centrifuging.

The present invention is concerned with the rheology of the low calorie fat materials at body temperature (98.6° F., 37° C.) because they must be stable and viscous at body temperature to eliminate a laxative side effect. However, the measurements herein were done at 100° F. (37.8° C.) as a matter of convenience and for easier calibration of instruments, and the invention is defined in terms of properties at 100° F. (37.8° C). It is understood that measurements done at 100° F. (37.8° C.) are very close to measurements at body temperature, and they conservatively state the rheological properties at body temperature since a lower temperature increases the viscosity.

The fat materials herein exhibit unexpected rheology and liquid/solid stability at body temperature. For example, specially synthesized intermediate melting sucrose fatty acid polyesters which are 12% solid and 88% liquid at body temperature exhibit non-Newtonian pseudoplastic flow properties, are very viscous and have excellent liquid/solid stability. This is in contrast to the properties of a mixture containing 88% of a liquid sucrose polyester and 12% of a solid sucrose polyester. At body temperature the mixture of 12% solid sucrose polyester and 88% liquid sucrose polyester separates into liquid and solid portions. Additionally, the mixture has a low viscosity. The specially synthesized sucrose polyesters, on the other hand, exhibit pseudoplastic flow and surprising viscosity and liquid/solid stability at relatively low levels of solids.

A benefit of the low calorie fat materials' high viscosity and liquid/solid stability is that ingestion of the materials does not result in an undesirable laxative side effect. Being viscous and stable, the materials pass from the digestive tract through the anal sphincter in much the same manner as normal feces. Hence, the materials of this invention can be safely ingested without adding anti-anal leakage agents.

Another benefit accrues from the fact that the present fat materials are able to retain their high viscosity and stability at relatively low solids content levels. When the compositions are ingested, less solids are perceived in the mouth, so the compositions taste less waxy.

The low calorie fat materials of this invention are thought to be homogenous systems. While not intending to be bound by theory, evidence of networking between the solid crystals and liquid of the materials has been discovered which may be involved in the surprisingly high liquid/solid stability and viscosity of the materials at body temperature.

The present invention, then, relates to a composition of matter comprising an edible, wholly or partially nondigestible low calorie fat material having physical chemical properties such that it has a non-Newtonian pseudoplastic rheology at 100° F. (37.8° C.). In particular, at 100° F. (37.8° C.) the fat material has: (a) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$; (b) a yield point of at least about 2,500 dynes/cm$^2$; (c) a thixotropic area of at least about 0.20×10$^6$ dynes/cm$^2$-sec.; and (d) a liquid/solid stability of at least about 50%.

It is believed that the viscosity at the lower shear rate of 10 seconds$^{-1}$ is the rheology specification that most closely simulates the forces on the low calorie fat materials during digestion.

Viscosity, yield point, and thixotropic area are well known rheological properties, and can be measured by use of an instrument such as a plate and cone viscometer (e.g., a Ferranti-Shirley viscometer, manufactured by Ferranti Electric, Inc., 87 Nodular Ave., Commack, N.Y. 11725). The basics of rheology are discussed in Idson, "Rheology: Fundamental Concepts," Cosmetics and Toiletries, Vol. 93, pp. 23–30 (July 1978). "Viscosity" is a measure of the internal friction resisting the movement of each layer of fluid as it moves past an adjacent layer of fluid. The "yield value" is the amount of shearing stress that must be applied before a material will begin to flow. Idson defines "thixotropy" as a reversible gel-sol-gel transition caused by the building up of a definite structure within the material. The gelled structure upon shaking or stirring becomes a sol, which when allowed to remain undisturbed, becomes gelled again.

To measure viscosity, yield point, and thixotropic area of a sample of the fat material of this invention, a plate and cone viscometer is used to record a rheogram, which is a plot of shear stress versus shear rate. Viscosity and yield point are calculated from points on the rheogram curve, and the thixotropic area is the area within the curve (also known as the "hysteresis loop"). The discussion of this method in Idson is incorporated herein by reference. Additional details are provided below under the Analytical Methods section.

Preferably, at 100° F. (37.8° C.) the low calorie fat materials of this invention have a viscosity of at least about 5 poise at a shear rate of 800 seconds$^{-1}$, a viscosity of at least about 20 poise at a shear rate of 100 seconds$^{-1}$, and a viscosity of at least about 200 poise at a shear rate of 10 seconds$^{-1}$. The preferred yield point of the compositions is at least about 5,000 dynes/cm$^2$, and the preferred thixotropic area is at least about 0.75×10$^6$ dynes/cm$^2$-sec. Preferably, the compositions have a liquid/solid stability of at least about 90%.

Most preferably, at 100° F. (37.8° C.) the low calorie fat materials have a viscosity of at least about 8 poise at a shear rate of 800 seconds$^{-1}$, a viscosity of at least about 30 poise at a shear rate of 100 seconds$^{-1}$, and a viscosity of at least about 400 poise at a shear rate of 10 seconds$^{-1}$. The most preferred yield point of the compositions is at least about 15,000 dynes/cm$^2$, and the most preferred thixotropic area is at least about $1.00 \times 10^6$ dynes/cm$^2$-sec.

The preferred upper limit of the viscosity of the fat materials of this invention is about $1 \times 10^5$ poise at a shear rate of 10 seconds$^{-1}$, and about 1,000 poise at a shear rate of 100 seconds$^{-1}$. The fat materials must have pseudoplastic flow properties as defined herein.

Iodine Value is a measure of the degree of unsaturation of fatty acids. The low calorie fat materials of this invention preferably have an Iodine Value of from about 36 to about 55.

The Solid Fat Content value (SFC) provides a reasonable approximation of the percent by weight solids of a particular fatty material at a given temperature. The present low calorie fat material preferably has a Solid Fat Content at 100° F. (37.8° C.) of at least about 5%. Most preferably, the Solid Fat Content at 100° F. (37.8° C.) is at least about 10%. The low calorie fat material preferably has a complete melting point higher than about 98.6° F. (37° C.).

The low calorie fat materials of the present invention can be any of a variety of edible, wholly or partially nondigestible compounds. Preferably, the fat material is selected from the group consisting of polyol fatty acid polyesters and polycarboxylic acids esterified with fatty alcohols, and mixtures thereof. Preferred polyol fatty acid polyesters are sugar fatty acid polyesters, sugar alcohol fatty acid polyesters, and polyglycerol fatty acid polyesters, and mixtures thereof. More preferably, the fat material is selected from the group consisting of sugar fatty acid polyesters and sugar alcohol fatty acid polyesters, and mixtures thereof, the sugars and sugar alcohols containing from 4 to 8 hydroxyl groups.

Sugar or sugar alcohol fatty acid polyesters comprise sugars or sugar alcohols, and fatty acids. The term "sugar" is used herein in its conventional sense as generic to mono- and disaccharides. The term "sugar alcohol" is also used in its conventional sense as generic to the reduction product of sugars wherein the aldehyde or ketone group has been reduced to an alcohol. The fatty acid ester compounds are prepared by reacting a monosaccharide, disaccharide or sugar alcohol with fatty acids as discussed below.

Examples of suitable monosaccharides are those containing 4 hydroxyl groups such as xylose, arabinose, and ribose; the sugar alcohol derived from xylose, i.e., xylitol, is also suitable. The monosaccharide erythrose is not suitable for the practice of this invention since it only contains 3 hydroxyl groups; however, the sugar alcohol derived from erythrose, i.e. erythritol, contains 4 hydroxyl groups and is thus suitable. Among 5 hydroxyl-containing monosaccharides that are suitable for use herein are glucose, mannose, galactose, fructose, and sorbose. A sugar alcohol derived from sucrose, glucose, or sorbose, e.g., sorbitol, contains 6 hydroxyl groups and is also suitable as the alcohol moiety of the fatty acid ester compound. Examples of suitable disaccharides are maltose, lactose, and sucrose, all of which contain 8 hydroxyl groups.

In preparing sugar or sugar alcohol fatty acid polyesters of the present invention a sugar or sugar alcohol compound such as those identified above must be esterified with a mixture of fatty acids having from about 8 to about 22 carbon atoms. Examples of such fatty acids are caprylic, capric, lauric, myristic, myristoleic, palmitic, palmitoleic, stearic, oleic, ricinoleic, linoleic, linolenic, eleostearic, arachidic, behenic, and erucic. The fatty acids can be derived from suitable naturally occurring or synthetic fatty acids and can be saturated or unsaturated, including positional and geometric isomers. The fat materials of this invention are mixed esters of fatty acids, rather than esters of a single type of fatty acid.

Fatty acids per se or naturally occurring fats and oils can serve as the source for the fatty acid component in the sugar or sugar alcohol fatty acid ester. For example, rapeseed oil provides a good source for $C_{22}$ fatty acid. $C_{16}$–$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component.

The sugar or sugar alcohol fatty acid polyesters suitable for use herein can be prepared by a variety of methods well known to those skilled in the art. These method include: transesterification of the sugar or sugar alcohol with methyl, ethyl or glycerol fatty acid esters using a variety of catalysts; acylation of the sugar or sugar alcohol with a fatty acid chloride; acylation of the sugar or sugar alcohol with a fatty acid anhydride; and acylation of the sugar or sugar alcohol with a fatty acid, per se. As an example, the preparation of sugar and sugar alcohol fatty acid esters is described in U.S. Pat. No. 2,831,854.

A characterizing feature of the sugar or sugar alcohol fatty acid polyesters useful in this invention is that they predominantly contain at least 4 fatty acid polyester groups. Sugar or sugar alcohol fatty acid polyester compounds that contain 3 or less fatty acid ester groups are digested in the intestinal tract much in the manner as ordinary triglyceride fats, but sugar or sugar alcohol fatty acid polyester compounds that contain four or more fatty acid ester groups are digested to a lesser extent and thus have the desired low calorie properties for use in this invention.

Highly preferred low calorie fat materials according to this invention are sucrose fatty acid polyesters. Preferred sucrose fatty acid polyesters have the majority of their hydroxyl groups esterified with fatty acids. Preferably at least about 85%, and most preferably at least about 95%, of the sucrose fatty acid polyesters are selected from the group consisting of octaesters, heptaesters and hexaesters, and mixtures thereof. Preferably, no more than about 35% of the esters are hexaesters or heptaesters, and at least about 60% of the sucrose fatty acid polyesters are octaesters. Most preferably, at least about 70% of the polyesters are octaesters.

In order to provide the required physical properties, the sucrose fatty acid polyesters of this invention are preferably esterified with particular kinds of fatty acids. Preferably, at least about 80%, and most preferably at least about 90%, of the fatty acids are selected from the group consisting of mixtures of palmitic, stearic, oleic, linoleic, and behenic acids.

More specifically, the following is a preferred fatty acid composition: from about 9% to about 12% palmitic; from about 35% to about 53% stearic; from about 19% to about 43% oleic; from about 2% to about 17% linoleic; from about 0% to about 2% linolenic; from about 0% to about 2% arachidic; from about 0% to about 10% behenic; and from about 0% to about 2% erucic.

The following fatty acid composition is most preferred: from about 9% to about 12% palmitic; from about 42% to about 53% stearic; from about 19% to about 39% oleic; from about 2% to about 17% linoleic; from about 0% to about 2% linolenic; from about 0% to about 2% arachidic; from about 0% to about 10% behenic; and from about 0% to bout 2% erucic.

Polyglycerol fatty acid polyesters can also be low calorie fat materials of the present invention. Polyglycerol is prepared by the polymerization of glycerine in the presence of either acid or base. The polyglycerols can contain from 2 to 20 glycerol moieties. Preferably, the polyglycerols will be those having from 2 to 15 glycerol moieties.

The polyglycerol compounds can be made by any synthetic method. See, for example, U.S. Pat. No. 3,968,169 to Seiden and Martin (1976). Esterification of the polyglycerols can also be done by any method known to the art, providing the resulting polyglycerol esters have the rheological properties required of the present invention.

Animal studies have now shown polyglycerol esters with the following Theological properties to be very effective at eliminating laxative side effect: (a) a viscosity of 3.13 poise at a shear rate of 800 seconds$^{-1}$, a viscosity of 5.18 poise at a shear rate of 100 seconds$^{-1}$, and a viscosity of 32.43 poise at a shear rate of 10 seconds$^{-1}$; (b) a thixotropic area of 0.246×10$^6$ dynes/cm$^2$-sec.; and (c) a liquid/solid stability of 53.45%.

The "polycarboxylic acids esterified with fatty alcohols" are tricarboxylic and tetracarboxylic acids and higher. The polycarboxylic acids can be partially or wholly esterified with fatty alcohols. At least three fatty alcohol ester groups must be on an acid molecule to make it partially nondigestible.

The low calorie fat materials of the present invention can be used as a partial or total replacement for normal triglyceride fat in any fat-containing food composition to provide low calorie benefits. Very low calorie and thus highly desirable food compositions of the invention are obtained when the fat comprises up to about 100% of the fat materials of this invention, and from 25% to 100% of the calories.

The present low calorie fat materials, and particularly sucrose polyesters, are useful in a wide variety of food and beverage products. For example, the fat materials can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

In addition to their uses in baked goods, the low calorie fat materials can be used alone or in combination with other regular, reduced calorie or zero calorie fats to make shortening and oil products. The other fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oils.

The present low calorie fat materials can also be fortified with vitamins and minerals, particularly the fat-soluble vitamins. The fat-soluble vitamins include vitamin A, vitamin D, vitamin E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. Vitamin D is a fat-soluble vitamin well known for use in the treatment and prevention of rickets and other skeletal disorders. "Vitamin D" comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are $K_1$ (phylloquinone), $K_2$ (menaquinone), and $K_3$ (menadione). The amount of the fat-soluble vitamins employed herein to fortify the present low calorie fat materials can vary. If desired, the fat materials can be fortified with a recommended daily allowance (RDA), or increment or multiple of an RDA, of any of the fat-soluble vitamins or combinations thereof.

Vitamins that are nonsoluble in fat can similarly be included in the present low calorie fat materials. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present low-calorie fat materials.

The present low calorie fat materials are particularly useful in combination with particular classes of food and beverage ingredients. For example, an extra calorie reduction benefit is achieved when the fat materials are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The low calorie fat materials can be used in combination with other noncaloric or reduced calorie fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the fat materials are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the low calorie fat materials in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

Similarly, food and beverage compositions can be made that combine the present low calorie fat materials with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for examples, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

Of course, judgment should be exercised to make use of appropriate low calorie fat materials and combinations of the fat materials with other food ingredients. For example, a combination of sweetener and fat material would not be used where the specific benefits of the two are not desired. The fat materials and fat material/ingredient combinations are used where appropriate, and in the proper amounts.

Many benefits are obtained from the use of the present low calorie fat materials in food and beverage compositions, either when used alone or in combination with the ingredients discussed above. A primary benefit is the calorie reduction achieved when the fat materials are used as a total or partial fat replacement. This calorie reduction can be increased by using combinations of the present fat materials with reduced calorie sweeteners, bulking agents, or other reduced calorie or noncaloric fats. Another benefit which follows from this use is a decrease in the total amount of fats in the diet. Foods or beverages made with the low calorie fat materials instead of triglyceride fats will also contain less cholesterol, and the ingestion of these foods can lead to reduced serum cholesterol and thus reduced risk of heart disease.

A related benefit is that the use of the low calorie fat materials allows the production of foods and beverages that are stable in terms of shelf stability and penetration stability. Compositions made with the fat materials have acceptable organoleptic properties, particularly taste and texture.

Dietary foods can be made with the low calorie fat materials, to meet special dietary needs, for example, of persons who are obese, diabetic, or hypercholesterolemic. The fat materials can be a major part of a low-fat, low-calorie, low-cholesterol diet, and they can be used alone or in combination with drug therapy or other therapy. Combinations of food or beverage products made with the low calorie fat materials can be used as part of a total dietary management regimen, based on one or more of these products, containing the fat materials alone or in combination with one or more of the above-mentioned ingredients, to provide one or more of the above-mentioned benefits.

This discussion of the low calorie fat material uses, combinations, and benefits, is not intended to be limiting or all-inclusive. It is contemplated that other similar uses and benefits can be found that will fall within the spirit and scope of this invention.

It is known that certain fatty esters will inhibit the absorption of cholesterol. The present invention also encompasses methods for lowering serum cholesterol by inhibiting the absorption of cholesterol without causing an anal leakage effect, comprising systemically (generally, orally) administering to animals susceptible to or afflicted with hypercholesterolemia successive therapeutically effective doses of the low calorie fat materials of the foregoing type. Generally the dosage is about 0.1 gram to about 5 grams of the present fat materials.

Analytical Methods

I. Rheology Measurements

A. Sample Preparation

The low calorie fat material is melted in a microwave oven at about 150° F. (66° C.) to about 170° F. (77° C.). This takes approximately 2 minutes. The melted fat material is held at 100° F. (37.8° C. ), and a 3 gram sample is weighed into a Solo$^R$ plastic souffle cup. The sample is then allowed to recrystallize at 100° F. 2 (37.8° C.1) for 24 hours. After the 24 hour time period has elapsed, the sample is taken to the viscometer in an insulated cup and the viscosity is measured.

B. Ferranti-Shirley Viscometer Operation Procedure

A Ferranti-Shirley viscometer is used for the viscosity, yield point, and thixotropic area measurements. A cone is put into place, and the viscometer temperature is adjusted to 100° F. (37.8° C.). The chart recorder is calibrated, and the gap between the cone and plate is set. The cone speed is checked, and the cone and plate temperatures are equilibrated to 100° F. (37.8° C.). The panel controls are set. Sufficient sample is placed between the plate and the cone so that the gap is completely filled. The temperature is allowed to stabilize at 100° F. (37.8° C.) for about 30 seconds, and then the cone rotation and recording are started. A rheogram for the fat material is recorded and analyzed to determine the viscosity, yield point, and thixotropic area. Viscosity is measured at shear rates of 800 seconds$^{-1}$, 100 seconds$^{-1}$, and 10 seconds$^{-1}$. The viscosities at 10 seconds$^{-1}$ and 100 seconds$^{-1}$ are determined from a line drawn from the viscosity at 800 seconds$^{-1}$ down the straight line portion of the increasing shear rate ramp.

II. Liquid/Solid Stability Measurement

The sample is heated until it completely melts and is thoroughly mixed. The sample is then poured into centrifuge tubes to capacity at 100° F. +5° F. (37.8° C. +3° C.). The samples then are allowed to recrystallize for 24 hours at 100° F. +5° F. (37.8° C. +3° C.). The samples are then centrifuged at 50,000 rpm [in a Beckman Model 1.8 70M centrifuge having a Beckman Model SW 60 head (Beckman Instruments, Palo Alto, Calif.)] for one hour at 100° F. (37° C.). [The minimum force on the samples is 254,000 g's, and the maximum force (i.e., the force at the bottom of the test tube) is 485,000 g's.] The force on the samples is 175,000 g's. The percent liquid separated is then measured by comparing the relative heights of the liquid and solid phases.

III. Solid Fat Content Measurement

Before determining SFC values, the fat material sample is heated to a temperature of 158° F. (70° C.) or higher for at least 0.5 hours or until the sample is completely melted. The melted sample is then tempered according to A.O.C.S. Official Method Cd 16-81. After tempering, the SFC value of the fat material at a temperature of 100° F. (37.8° C.) and after desired temperatures is determined by pulsed nuclear magnetic resonance (PNMR). The method for determining SFC values of a fat by PNMR is described in Madison and Hill, *J. Amer. Oil. Chem. Soc.*, Vol. 55 (1978), pp. 328–31 and A.C.S. Official Method Cd 16–18 (herein incorporated by reference).

The following Examples are intended to be further illustrative but not limiting of the present invention.

EXAMPLE 1

Methyl esters of a fully hydrogenated soy oil and a touch-hardened soy oil, blended in a 55/45 ratio (16 kg), and 2 kg. of an 15 wt. percent solution of potassium hydroxide in methanol are mixed in a stainless steel batch reactor. This mixture is then heated to 86° F. (30° C.) with agitation for 1 to 2 hours at atmospheric pressure. During this time, a portion of the methyl esters are saponified. A vacuum is then pulled on the system to remove the last traces of methanol.

Powdered sucrose (3 kg.) is added to the soap/ester mixture to give a 5:1 molar ratio of ester to sucrose. Potassium carbonate is then added to the mixture (approx. 0.5 wt. percent of the reaction mix) to catalyze the transesterification. This mixture is agitated and heated under vacuum at about 275° F. (135° C.) for up to 2½ hours to form the mono-, di- and trisucrose esters. Small quantities of tetra- and pentaesters are also formed during this stage. Additional methyl ester (19.5 kg) which has been preheated to 275° F. (135° C.) is added to bring and maintain the molar ratio of the esters to sucrose to 12:1. When the reaction conditions stabilize at 275° F. (135° C.), a nitrogen sparge is used to improve agitation and promote methanol stripping. As the reaction occurs, the reaction mixture becomes viscous and then thins out. This second reaction stage lasts approximately 4 to 8 hours.

After the reaction mixture has become thin, it is cooled to between 149° F. (65° C.) and 185° F. (85° C.). The crude reaction mixture is agitated with a dilute solution of methanol, sodium chloride and water. The volume of this wash solution is equal to 20% to 40% of the reaction mixture volume. The mixed phases are then allowed to settle for approximately 30 to 60 minutes. The lower settled phase which contains the soaps, excess sugars and methanol is drawn off and discarded. The upper settled phase which comprises the refined sucrose polyesters is washed again. Usually 2 to 4 washes are used.

The sucrose polyesters are then washed with a 1% glacial acetic acid in water solution at 10% to 20% of the volume of the reaction mix. This is followed by water wash of the same volume.

The reaction mix is then dried to remove moisture at 176° F. (80° C.) under 10 mm Hg or less vacuum for 30 to 60 minutes. Filtrol 105 (0.5 wt. percent), and a filter aid (0.5 wt. percent) are added and the mix is agitated at 167° F. (75° C.) to 185° F. (85° C.). The slurry is separated by filtration or other means until there is less than 0.1 wt. percent fines. The liquid is then passed through a 1 micromillimeter filter.

The refined and bleached reaction mix is put into a stainless steel batch deodorizer to distill off the bulk of the methyl esters. The distillation takes place at 374° F. (190° C.) to 482° F. (250° C.) under approximately 5 mm Hg of vacuum. This step is complete when it is visually evident that the distillation has slowed down.

The sucrose polyester is then deodorized in a stainless steel batch deodorizer or other suitable device at 374° F. (190° C.) to 482° F. (250° C.) under a vacuum of about 5 mm Hg with steam sparging. Deodorization is continued until the methyl ester content is below 200 ppm. The deodorizer contents are then cooled while using inert gas sparging. After cooling to 149° F. (65° C.), the deodorizer is brought to atmospheric pressure. The sucrose polyester is stored in clean stainless steel drums.

This produces a sucrose polyester product having the fatty acid composition specified in Table I. Rheology and effectiveness at preventing laxative side effect are listed in Table II.

The results shown in Tables I and II illustrate that sucrose polyesters prepared according to Example 1 have the properties of the low calorie fat materials of the present invention. The third column in Table I shows the properties of a liquid sucrose polyester prepared according to a method known to the art, and not falling within the present invention.

Table II compares the rheology and effectiveness at preventing laxative side effect of the two samples. Example 1 has rheological properties according to this invention; the liquid sucrose polyester does not. The liquid sucrose polyester results in a 15% oil loss when ingested. By contrast, the sucrose polyesters prepared in Example 1 result in 0% oil loss, showing that they are very effective at eliminating laxative side effect.

TABLE I

Sucrose Polyester Composition

| | Example 1 | Liquid Sucrose Polyester |
|---|---|---|
| Fatty Acid Composition | % | % |
| Others | 2.6 | 3.4 |
| $C_{16}$ | 9.4 | 8.6 |
| $C_{18}$ | 51.8 | 5.7 |
| $C_{18:1}$ | 20.4 | 45.6 |
| $C_{18:2}$ | 15.8 | 31.7 |
| $C_{18:3}$ | 0 | 0.4 |
| $C_{20}$ | 0 | 0.6 |
| $C_{22}$ | 0 | 0.0 |
| I.V. | 47.6 | 100 |
| Ester Distribution | % | % |
| Octa | 79.0 | 71.1 |
| Hepta | 19.2 | 24.0 |
| Hexa | 1.8 | 4.9 |
| Penta | 0.1 | 0.1 |
| < Penta | 0.1 | 0.1 |
| SFC Profile | % | % |
| 50 F. | 64.3 | 0 |
| 70 F. | 53.6 | 0 |
| 80 F. | 43.0 | 0 |
| 92 F. | 21.1 | 0 |
| 105 F. | 2.7 | 0 |
| 98.6 F. | 11.9 | 0 |
| DSC Behavior | C. | C. |
| Complete Melt Point | 42.5 | −20.0 |
| Maximum Melt Point | 39.4 | −35.0 |
| Heat of Fusion | 11.7 cal./g. | 10.6 cal./g. |

TABLE II

Comparison of Physical Properties of the
Sucrose Polyesters with Effectiveness Against Laxative Side Effect

|  | LSE Effectiveness | Rheology | | | | | Liq/Solid |
|---|---|---|---|---|---|---|---|
|  |  | Viscosity (poise) | | | | Thixotropic |  |
|  | Oil Loss (%) | 800 (sec.$^{-1}$) | 100 (sec.$^{-1}$) | 10 (sec.$^{-1}$) | Yield Point (dynes/cm$^2$) | Area (dynes/cm$^2$-sec.) | Stability (100%-% Sep.) |
| EFFECTIVE: |  |  |  |  |  |  |  |
| Example 1 | 0 | 8.2 | 38.9 | 370 | 13,997 | 1.324 × 10$^6$ | 100 |
| INEFFECTIVE: |  |  |  |  |  |  |  |
| Liquid Sucrose Polyester | 15 | 2.1 | 2.1 | 2 | None | None | -NA- |

What is claimed is:

1. A low calorie fat composition comprising an edible, wholly or partially nondigestible low calorie fat material selected from the group consisting of sucrose fatty acid polyesters with an octaesters content of at least about 60%, xylose fatty acid polyesters, arabinose fatty acid polyesters, ribose fatty acid polyesters, glucose fatty acid polyesters, mannose fatty acid polyesters, galactose fatty acid polyesters, fructose fatty acid polyesters, sorbose fatty acid polyesters, maltose fatty acid polyesters, lactose fatty acid polyesters, sugar alcohol fatty acid polyesters, and mixtures thereof, wherein the sugar alcohols contain from 4 to 8 hydroxyl groups, wherein the fatty acid polyesters have at least 4 fatty acid ester groups, wherein the fatty acids are mixtures of fatty acids selected from the group of fatty acids containing from about 8 to about 22 carbon atoms, and wherein the fat material has:
   (i) at 100° F. (37.8° C.), a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$;
   (ii) at 100° F. (37.8° C.), a liquid/solid stability of at least about 50%; and
   (iii) at 92° F. (33.3° C.), a solid fat content of not more than about 21%.

2. A low calorie fat composition comprising an edible, wholly or partially nondigestible low calorie fat material selected from the group consisting of sucrose fatty acid polyesters with an octaesters content of at least about 60%, xylose fatty acid polyesters, arabinose fatty acid polyesters, ribose fatty acid polyesters, glucose fatty acid polyesters, mannose fatty acid polyesters, galactose fatty acid polyesters, fructose fatty acid polyesters, sorbose fatty acid polyesters, maltose fatty acid polyesters, lactose fatty acid polyesters, sugar alcohol fatty acid polyesters, and mixtures thereof, wherein the sugar alcohols contain from 4 to 8 hydroxyl groups, wherein the fatty acid polyesters have at least 4 fatty acid ester groups, wherein the fatty acids are mixtures of fatty acids selected from the group of fatty acids containing from about 8 to about 22 carbon atoms, and wherein the fat material has:
   (i) at 100° F. (37.8° C.), a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$;
   (ii) at 100° F. (37.8° C.), a liquid/solid stability of at least about 50%; and
   (iii) at 98.6° F. (37° C.), a solid fat content of not more than about 12%.

3. A low calorie fat composition comprising an edible, wholly or partially nondigestible low calorie fat material selected from the group consisting of sucrose fatty acid polyesters with an octaesters content of at least about 70%, xylose fatty acid polyesters, arabinose fatty acid polyesters, ribose fatty acid polyesters, glucose fatty acid polyesters, mannose fatty acid polyesters, galactose fatty acid polyesters, fructose fatty acid polyesters, sorbose fatty acid polyesters, maltose fatty acid polyesters, lactose fatty acid polyesters, sugar alcohol fatty acid polyesters, and mixtures thereof, wherein the sugar alcohols contain from 4 to 8 hydroxyl groups, wherein the fatty acid polyesters have at least 4 fatty acid ester groups, wherein the fatty acids are mixtures of fatty acids selected from the group of fatty acids containing from about 8 to about 22 carbon atoms, and wherein the fat material has, at 100° F. (37.8° C.):
   (i) a viscosity of at least about 2.5 poise at a shear rate of 800 seconds$^{-1}$, a viscosity of at least about 4.0 poise at a shear rate of 100 seconds$^{-1}$, and a viscosity of at least about 15.0 poise at a shear rate of 10 seconds$^{-1}$; and
   (ii) a liquid/solid stability of at least about 90%.

4. A composition according to any of claim 1, 2 or 3 having a viscosity of at least about 5 poise at a shear rate of 800 seconds$^{-1}$, a viscosity of at least about 20 poise at a shear rate of 100 seconds$^{-1}$, and a viscosity of at least about 200 poise at a shear rate of 10 seconds$^{-1}$.

5. A composition according to claim 4 having a liquid/solid stability of at least about 90%.

6. A composition according to any of claims 1,3 having an Iodine Value of from about 36 to about 55.

7. A composition according to any of claims 1,3 having a Solid Fat Content at 100° F. (37.8° C.) of at least about 5%.

8. A composition according to any of claims 1,3 wherein the fat materials comprise sucrose fatty acid polyesters.

9. A composition according to claim 8 wherein at least about 80% of the fatty acids are selected from the group consisting of mixtures of palmitic, stearic, oleic, linoleic and behenic acids.

10. A composition according to claim 9 wherein at least about 90% of the fatty acids are selected from the group consisting of mixtures of palmitic, stearic, oleic, linoleic and behenic acids.

11. A composition according to claim 10 having the following fatty acid composition: from about 9% to about 12% palmitic; from about 35% to about 53% stearic; from about 19% to about 43% oleic; from about 2% to about 17% linoleic; from about 0% to about 2% linolenic, from about 0% to about 2% arachidic, from about 0% to about 10% behenic, and from about 0% to about 2% erucic.

12. A composition according to claim 11 having the following fatty acid composition: from about 9% to about 12% palmitic; from about 42% to about 53% stearic; from about 19% to about 39% oleic; from about 2% to about 17% linoleic; from about 0% to about 2% linolenic; from about 0% to about 2% arachidic, from about 0% to about 10% behenic, and from about 0% to about 2% erucic.

13. A composition according to any of claims 1,3 additionally comprising fat-soluble vitamins.

14. A food composition comprising non-fat ingredients and fat ingredients, wherein up to about 100% of the total fat ingredients is a composition according to any of claim 1, 2 or 3, and wherein the food is selected from the group consisting of margarine, shortening, cooking oil, salad dressing, cookies and cake.

15. A composition according to any of claim 1, 2 or 3, wherein the low calorie fat material additionally has, at 100° F. (37.8° C.), a yield point of at least about 2,500 dynes/cm².

16. A composition according to any of claim 1, 2 or 3, wherein the low calorie fat material additionally has, at 100° F. (37.8° C.), a thixotropic area of at least about $0.20 \times 10^6$ dynes/cm²-second.

17. A composition according to any of claim 1, 2 or 3 wherein the low calorie fat material additionally has a viscosity at 100° F. (37.8° C.) of not more than about 100,000 poise at a shear rate of 10 seconds$^{-1}$.

18. A composition of matter comprising an edible, low calorie material, wherein the low calorie material has:
  (i) at 100 degrees Fahrenheit a viscosity of at least about 2.5 poise at a shear rate of 800/second, a viscosity of at least about 4.0 poise at a shear rate of 100/second, and a viscosity of at least about 15.0 poise at a shear rate of 10/second;
  (ii) at 100 degrees Fahrenheit a liquid/solid stability of at least about 90%;
  (iii) at 92 degrees Fahrenheit a solid fat content of not more than about 21%;
  (iv) at 98.6 degrees Fahrenheit a solid fat content of not more than about 12%; and
  (v) at 100 degrees Fahrenheit a Thixotropic area of at least about 200,000 dynes/(square centimeter-second).

* * * * *